US010173687B2

(12) United States Patent
Sham

(10) Patent No.: US 10,173,687 B2
(45) Date of Patent: Jan. 8, 2019

(54) METHOD FOR RECOGNIZING VEHICLE DRIVER AND DETERMINING WHETHER DRIVER CAN START VEHICLE

(71) Applicant: Wellen Sham, Taipei (TW)

(72) Inventor: Wellen Sham, Taipei (TW)

(73) Assignee: Wellen Sham, Taipei (TW)

( * ) Notice: Subject to any disclaimer, the term of this patent is extended or adjusted under 35 U.S.C. 154(b) by 0 days.

(21) Appl. No.: 15/063,435

(22) Filed: Mar. 7, 2016

(65) Prior Publication Data
US 2016/0272214 A1 Sep. 22, 2016

Related U.S. Application Data

(60) Provisional application No. 62/272,706, filed on Dec. 30, 2015, provisional application No. 62/150,848, (Continued)

(51) Int. Cl.
*B60W 40/08* (2012.01)
*A61B 5/00* (2006.01)
(Continued)

(52) U.S. Cl.
CPC ......... *B60W 40/08* (2013.01); *A61B 5/02055* (2013.01); *A61B 5/1172* (2013.01);
(Continued)

(58) Field of Classification Search
CPC .................. B60W 50/08; B60W 50/14; B60W 2050/143; B60W 2050/146; B60W 40/08;
(Continued)

(56) References Cited

U.S. PATENT DOCUMENTS 3,723,215 A  3/1973 Kessler
4,007,315 A  2/1977 Brinkmann et al.
(Continued)

FOREIGN PATENT DOCUMENTS

AU  2008200543 A1  8/2009
CN  201761472 U  3/2011
(Continued)

OTHER PUBLICATIONS

Extended European Search Report dated Jul. 28, 2016 for EP 16160393.1, all pages.
(Continued)

*Primary Examiner* — Nga X Nguyen
(74) *Attorney, Agent, or Firm* — Kilpatrick Townsend & Stockton LLP

(57) ABSTRACT

Provided are systems and methods for increasing vehicle safety by determining whether a driver can operate a vehicle based on whether the physical status of the driver and the identity of the driver are acceptable. A first set of sensors may determine the physical status of the driver. The first set of sensors may include an electrocardiogram detection component, an alcohol detection component, a body temperature detection component, and a photography component, among others. A second set of sensors may determine the identity of the driver. The second set of sensors may a fingerprint detection component, an electrocardiogram detection component, and a photography component, among others. When it is determined that the physical status of the driver is unacceptable, the method may include activating an automatic driving system.

20 Claims, 9 Drawing Sheets

Related U.S. Application Data filed on Apr. 22, 2015, provisional application No. 62/133,991, filed on Mar. 16, 2015.

(51) Int. Cl.

| | | |
|---|---|---|
| *A61B 5/0205* | (2006.01) | |
| *A61B 5/1172* | (2016.01) | |
| *B60R 1/00* | (2006.01) | |
| *B60R 25/10* | (2013.01) | |
| *B60W 30/18* | (2012.01) | |
| *B60W 50/14* | (2012.01) | |
| *B60K 28/06* | (2006.01) | |
| *A61B 5/01* | (2006.01) | |
| *A61B 5/0452* | (2006.01) | |
| *A61B 5/08* | (2006.01) | |
| *A61B 5/11* | (2006.01) | |

(52) U.S. Cl.
CPC ............ *A61B 5/6893* (2013.01); *B60K 28/06* (2013.01); *B60R 1/00* (2013.01); *B60R 25/10* (2013.01); *B60W 30/18* (2013.01); *B60W 50/14* (2013.01); *A61B 5/01* (2013.01); *A61B 5/0452* (2013.01); *A61B 5/082* (2013.01); *A61B 5/1103* (2013.01); *B60R 2300/8006* (2013.01); *B60W 2040/0809* (2013.01); *B60W 2040/0827* (2013.01); *B60W 2040/0836* (2013.01); *B60W 2040/0872* (2013.01); *B60W 2050/143* (2013.01); *B60W 2540/22* (2013.01); *B60W 2540/24* (2013.01); *B60W 2540/26* (2013.01); *B60W 2540/28* (2013.01)

(58) Field of Classification Search
CPC ......... B60W 30/18; B60W 2040/0809; B60W 2040/0827; B60W 2040/0836; B60W 2040/0872; B60W 2540/22; B60W 2540/24; B60W 2540/26; B60K 2350/2013; B60K 28/06; H04L 43/06; B60R 25/10; B60R 1/00; B60R 2300/8006; A61B 5/02055; A61B 5/6893; A61B 5/1172; A61B 5/00; A61B 5/0205; A61B 5/0452
USPC ........................................ 701/1, 2, 36, 39, 45
See application file for complete search history.

(56) References Cited

U.S. PATENT DOCUMENTS

| | | | |
|---|---|---|---|
| 4,026,468 A | 5/1977 | Tinder et al. | |
| 4,079,275 A | 3/1978 | Fu | |
| 4,248,383 A | 2/1981 | Savage et al. | |
| 4,281,276 A | 7/1981 | Cutler et al. | |
| 4,324,363 A | 4/1982 | Rauen, Jr. | |
| 4,693,652 A | 9/1987 | Sweeney | |
| 4,848,835 A | 7/1989 | DeRees | |
| 4,926,105 A | 5/1990 | Mischenko et al. | |
| 5,115,342 A | 5/1992 | Rowe et al. | |
| 5,121,044 A | 6/1992 | Goldman | |
| 5,289,890 A | 3/1994 | Toyoda et al. | |
| 5,345,155 A | 9/1994 | Masaki et al. | |
| 5,585,204 A | 12/1996 | Oshida et al. | |
| 5,619,784 A | 4/1997 | Nishimoto et al. | |
| 5,666,040 A | 9/1997 | Bourbeau | |
| 5,710,504 A | 1/1998 | Pascual et al. | |
| 5,830,308 A | 11/1998 | Reichard | |
| 5,875,691 A | 3/1999 | Hata et al. | |
| 5,889,342 A | 3/1999 | Hasebe et al. | |
| 5,969,624 A | 10/1999 | Sakai | |
| 6,089,034 A | 7/2000 | Lake et al. | |
| 6,126,219 A | 10/2000 | Wilkinson et al. | |
| 6,272,809 B1 | 8/2001 | Wycech | |
| 6,335,078 B2 | 1/2002 | Venkataramani et al. | |
| 6,347,528 B1 | 2/2002 | Iritani et al. | |
| 6,357,541 B1 | 3/2002 | Matsuda et al. | |
| 6,367,570 B1 | 4/2002 | Long, III et al. | |
| 6,450,275 B1 | 9/2002 | Gabriel et al. | |
| 6,481,230 B2 | 11/2002 | Kimishima et al. | |
| 6,504,344 B1 | 1/2003 | Adams et al. | |
| 6,575,258 B1 | 6/2003 | Clemmer | |
| 6,766,036 B1 | 7/2004 | Pryor | |
| 6,772,504 B2 | 8/2004 | Weidman et al. | |
| 6,899,377 B2 | 5/2005 | Ghuman et al. | |
| 6,933,076 B2 | 8/2005 | Ura et al. | |
| 7,208,854 B1 | 4/2007 | Saban et al. | |
| 7,230,404 B2 | 6/2007 | Kimoto et al. | |
| 7,289,645 B2 | 10/2007 | Yamamoto et al. | |
| 7,325,866 B2 | 2/2008 | Horton et al. | |
| 7,332,242 B2 | 2/2008 | Sato et al. | |
| 7,335,205 B2 | 2/2008 | Aeschlimann et al. | |
| 7,436,139 B2 | 10/2008 | Maslov et al. | |
| 7,451,808 B2 | 11/2008 | Busse et al. | |
| 7,789,176 B2 | 9/2010 | Zhou | |
| 7,834,500 B2 | 11/2010 | Savant | |
| 7,841,431 B2 | 11/2010 | Zhou | |
| 8,020,656 B2 | 9/2011 | Inoue et al. | |
| 8,159,191 B2 | 4/2012 | Chang et al. | |
| 8,191,618 B2 | 6/2012 | Gering et al. | |
| 8,336,319 B2 | 12/2012 | Johnston et al. | |
| 8,344,849 B2 | 1/2013 | Larsson et al. | |
| 8,450,888 B2 | 5/2013 | Shafer et al. | |
| 8,479,855 B2 | 7/2013 | Kim et al. | |
| 8,527,130 B2 | 9/2013 | Kitahata et al. | |
| 8,556,558 B1 | 10/2013 | Hunt | |
| 8,564,246 B2 | 10/2013 | Wade et al. | |
| 8,571,738 B1 | 10/2013 | Potter et al. | |
| 8,625,855 B2 | 1/2014 | El Dokor | |
| 8,641,133 B1 | 2/2014 | Scaringe et al. | |
| 8,796,881 B2 | 8/2014 | Davis | |
| 8,798,832 B2 | 8/2014 | Kawahara et al. | |
| 8,818,716 B1 | 8/2014 | El Dokor et al. | |
| 8,892,281 B2 | 11/2014 | Suzuki et al. | |
| 8,896,167 B2 | 11/2014 | McKinzie et al. | |
| 8,955,345 B2 | 2/2015 | Meitinger et al. | |
| 8,983,718 B2 | 3/2015 | Ricci | |
| 8,985,680 B2 | 3/2015 | Mildner | |
| 9,144,389 B2 * | 9/2015 | Srinivasan ........... A61B 5/0408 | |
| 9,180,753 B2 | 11/2015 | Kim et al. | |
| 9,250,020 B2 | 2/2016 | Vikstrom et al. | |
| 9,469,350 B2 | 10/2016 | Wu | |
| 2002/0005440 A1 | 1/2002 | Holt et al. | |
| 2002/0134857 A1 | 9/2002 | Zimmer | |
| 2002/0182493 A1 | 12/2002 | Ovshinsky et al. | |
| 2003/0155001 A1 | 8/2003 | Hoetzer et al. | |
| 2004/0080218 A1 | 4/2004 | Weidman et al. | |
| 2004/0113589 A1 | 6/2004 | Crisp et al. | |
| 2004/0195833 A1 | 10/2004 | Zoellner | |
| 2004/0243013 A1 | 12/2004 | Kawachi et al. | |
| 2005/0206511 A1 | 9/2005 | Heenan et al. | |
| 2006/0021811 A1 | 2/2006 | Kuang et al. | |
| 2006/0132101 A1 | 6/2006 | Ambrosio et al. | |
| 2006/0175995 A1 | 8/2006 | Shinmura et al. | |
| 2006/0211364 A1 | 9/2006 | Brotz et al. | |
| 2007/0009787 A1 | 1/2007 | Straubel et al. | |
| 2007/0077541 A1 | 4/2007 | Champagne et al. | |
| 2007/0084484 A1 | 4/2007 | Porter et al. | |
| 2007/0261787 A1 | 11/2007 | Malis | |
| 2007/0265540 A1 * | 11/2007 | Fuwamoto ......... A61B 5/04525 600/515 |
| 2007/0278325 A1 | 12/2007 | Sato et al. | |
| 2008/0024020 A1 | 1/2008 | Iund et al. | |
| 2008/0042493 A1 | 2/2008 | Jacobs | |
| 2008/0067965 A1 | 3/2008 | Bailey et al. | |
| 2008/0116379 A1 | 5/2008 | Teder | |
| 2008/0210780 A1 | 9/2008 | Discher et al. | |
| 2008/0228365 A1 | 9/2008 | White et al. | |
| 2009/0023056 A1 | 1/2009 | Adams et al. | |
| 2009/0139781 A1 | 6/2009 | Straubel et al. | |
| 2009/0146610 A1 | 6/2009 | Trigiani | |
| 2009/0153087 A1 | 6/2009 | Lim et al. | |

(56) References Cited

U.S. PATENT DOCUMENTS

| | | | |
|---|---|---|---|
| 2009/0164069 A1* | 6/2009 | Yanagisawa | B60K 28/063 701/45 |
| 2009/0206689 A1 | 8/2009 | Harada et al. | |
| 2009/0230921 A1 | 9/2009 | Hsu et al. | |
| 2009/0250533 A1 | 10/2009 | Akiyama et al. | |
| 2009/0278915 A1 | 11/2009 | Kramer et al. | |
| 2010/0152936 A1 | 6/2010 | Wang et al. | |
| 2010/0230991 A1 | 9/2010 | Fioravanti | |
| 2010/0274480 A1 | 10/2010 | McCall et al. | |
| 2011/0031921 A1 | 2/2011 | Han | |
| 2011/0073142 A1 | 3/2011 | Hattori et al. | |
| 2011/0128543 A1 | 6/2011 | Choi | |
| 2011/0128555 A1 | 6/2011 | Rotschild et al. | |
| 2011/0159340 A1 | 6/2011 | Hu et al. | |
| 2011/0229749 A1 | 9/2011 | Kim et al. | |
| 2011/0246005 A1 | 10/2011 | King et al. | |
| 2011/0266375 A1 | 11/2011 | Ono et al. | |
| 2011/0292212 A1 | 12/2011 | Tanabe et al. | |
| 2011/0309796 A1 | 12/2011 | Firehammer | |
| 2012/0070701 A1 | 3/2012 | Gaben | |
| 2012/0081267 A1 | 4/2012 | Sirpal et al. | |
| 2012/0091964 A1 | 4/2012 | Vance et al. | |
| 2012/0101690 A1 | 4/2012 | Srinivasan et al. | |
| 2012/0105001 A1 | 5/2012 | Gallegos et al. | |
| 2012/0116699 A1 | 5/2012 | Haag et al. | |
| 2012/0163657 A1 | 6/2012 | Shellshear | |
| 2012/0168125 A1 | 7/2012 | Johnston et al. | |
| 2012/0222833 A1 | 9/2012 | Vikstrom et al. | |
| 2012/0231316 A1 | 9/2012 | Sohn | |
| 2012/0245763 A1 | 9/2012 | Mizuno | |
| 2012/0266922 A1 | 10/2012 | Krahn et al. | |
| 2012/0291987 A1 | 11/2012 | Himmer et al. | |
| 2012/0297809 A1 | 11/2012 | Carpenter | |
| 2012/0303397 A1 | 11/2012 | Prosser | |
| 2012/0313562 A1 | 12/2012 | Murao et al. | |
| 2013/0038151 A1 | 2/2013 | Ohashi et al. | |
| 2013/0057117 A1 | 3/2013 | Suzuki et al. | |
| 2013/0061630 A1 | 3/2013 | Schaefer et al. | |
| 2013/0070043 A1 | 3/2013 | Geva et al. | |
| 2013/0092758 A1 | 4/2013 | Tanaka et al. | |
| 2013/0094086 A1 | 4/2013 | Bochenek | |
| 2013/0117963 A1 | 5/2013 | Liu | |
| 2013/0124038 A1* | 5/2013 | Naboulsi | G08B 21/06 701/36 |
| 2013/0136975 A1 | 5/2013 | Uchida | |
| 2013/0144470 A1* | 6/2013 | Ricci | G06F 9/54 701/2 |
| 2013/0153338 A1 | 6/2013 | Yamauchi | |
| 2013/0179061 A1 | 7/2013 | Gadh et al. | |
| 2013/0217409 A1 | 8/2013 | Bridges et al. | |
| 2013/0221926 A1 | 8/2013 | Furtner | |
| 2013/0235381 A1 | 9/2013 | Kroekel et al. | |
| 2013/0249317 A1 | 9/2013 | Kang et al. | |
| 2014/0009615 A1 | 1/2014 | Kiyohara et al. | |
| 2014/0017528 A1 | 1/2014 | Yuji et al. | |
| 2014/0021924 A1 | 1/2014 | Abe et al. | |
| 2014/0033865 A1 | 2/2014 | Suzuki et al. | |
| 2014/0067323 A1 | 3/2014 | Skelton | |
| 2014/0070013 A1 | 3/2014 | Stanek et al. | |
| 2014/0077631 A1 | 3/2014 | Watanabe et al. | |
| 2014/0081521 A1 | 3/2014 | Frojdh et al. | |
| 2014/0089864 A1 | 3/2014 | Cheng et al. | |
| 2014/0090673 A1 | 4/2014 | Atsumi et al. | |
| 2014/0121927 A1 | 5/2014 | Hanita | |
| 2014/0124159 A1 | 5/2014 | Kim | |
| 2014/0141300 A1 | 5/2014 | Ronning et al. | |
| 2014/0145933 A1 | 5/2014 | Chae et al. | |
| 2014/0167655 A1 | 6/2014 | Chatroux et al. | |
| 2014/0203782 A1 | 7/2014 | Xue et al. | |
| 2014/0216709 A1 | 8/2014 | Smith et al. | |
| 2014/0223384 A1 | 8/2014 | Graumann | |
| 2014/0247135 A1* | 9/2014 | Proud | H02J 17/00 340/870.01 |
| 2014/0277936 A1 | 9/2014 | El Dokor et al. | |
| 2014/0282271 A1 | 9/2014 | Lu et al. | |
| 2014/0306826 A1 | 10/2014 | Ricci | |
| 2014/0309849 A1 | 10/2014 | Ricci | |
| 2014/0311704 A1 | 10/2014 | Yokoyama et al. | |
| 2014/0333161 A1 | 11/2014 | Knoblauch | |
| 2014/0354291 A1 | 12/2014 | Kikuchi et al. | |
| 2014/0356652 A1 | 12/2014 | Boddakayala et al. | |
| 2014/0365792 A1 | 12/2014 | Yun | |
| 2015/0008931 A1 | 1/2015 | Sugeno et al. | |
| 2015/0022664 A1 | 1/2015 | Pflug et al. | |
| 2015/0025917 A1 | 1/2015 | Stempora | |
| 2015/0044522 A1 | 2/2015 | Camp et al. | |
| 2015/0054933 A1 | 2/2015 | Wasiek et al. | |
| 2015/0069974 A1 | 3/2015 | Okada et al. | |
| 2015/0081135 A1 | 3/2015 | Gompert et al. | |
| 2015/0088397 A1 | 3/2015 | Burton | |
| 2015/0091698 A1 | 4/2015 | Du | |
| 2015/0138357 A1 | 5/2015 | Romack et al. | |
| 2015/0141043 A1 | 5/2015 | Abramson | |
| 2015/0017642 A1 | 6/2015 | Kato | |
| 2015/0151722 A1 | 6/2015 | Gokan et al. | |
| 2015/0168174 A1 | 6/2015 | Abramson | |
| 2015/0171642 A1 | 6/2015 | Kato et al. | |
| 2015/0188334 A1 | 7/2015 | Dao et al. | |
| 2015/0203077 A1 | 7/2015 | Gokan | |
| 2015/0317527 A1 | 11/2015 | Graumann et al. | |
| 2015/0367859 A1 | 12/2015 | Roth et al. | |
| 2016/0001330 A1 | 1/2016 | Romack et al. | |
| 2016/0048725 A1 | 2/2016 | Holz et al. | |
| 2016/0056510 A1 | 2/2016 | Takeuchi et al. | |
| 2016/0086391 A1 | 3/2016 | Ricci | |
| 2016/0187879 A1* | 6/2016 | Mere | G05D 1/0061 701/23 |
| 2016/0271905 A1 | 9/2016 | Lo | |
| 2016/0271926 A1 | 9/2016 | Lo | |
| 2016/0272036 A1 | 9/2016 | Chen et al. | |
| 2016/0272039 A1 | 9/2016 | Cheng | |
| 2016/0272040 A1 | 9/2016 | Cheng | |
| 2016/0272043 A1 | 9/2016 | Cheng | |
| 2016/0272044 A1 | 9/2016 | Cheng | |
| 2016/0272045 A1 | 9/2016 | Chen et al. | |
| 2016/0272082 A1 | 9/2016 | Chuang | |
| 2016/0272084 A1 | 9/2016 | Chuang | |
| 2016/0272085 A1 | 9/2016 | Dai | |
| 2016/0272087 A1 | 9/2016 | Lai | |
| 2016/0272164 A1 | 9/2016 | Hsiao et al. | |
| 2016/0272165 A1 | 9/2016 | Hsiao et al. | |
| 2016/0272242 A1 | 9/2016 | Sham | |
| 2016/0272254 A1 | 9/2016 | Wu | |
| 2016/0274668 A1 | 9/2016 | Hsaio et al. | |
| 2016/0274669 A1 | 9/2016 | Hsiao et al. | |
| 2016/0276638 A1 | 9/2016 | Sham | |
| 2016/0276721 A1 | 9/2016 | Ho | |
| 2016/0276722 A1 | 9/2016 | Ho | |
| 2016/0276854 A1 | 9/2016 | Lai | |
| 2016/0276855 A1 | 9/2016 | Lian | |
| 2016/0276903 A1 | 9/2016 | Lai | |
| 2016/0276905 A1 | 9/2016 | Lai | |
| 2016/0276963 A1 | 9/2016 | Lai | |

FOREIGN PATENT DOCUMENTS

| | | |
|---|---|---|
| CN | 102079245 A | 6/2011 |
| DE | 3837701 A1 | 5/1990 |
| DE | 10 2007 046037 B3 | 4/2009 |
| EP | 1 386 828 A2 | 2/2004 |
| EP | 1 990 849 A1 | 11/2008 |
| EP | 2 565 959 A2 | 6/2013 |
| EP | 2725684 A1 | 4/2014 |
| EP | 2949520 A1 | 12/2015 |
| JP | 3331529 B2 | 10/1994 |
| JP | 11-353598 A | 12/1999 |
| JP | 2007253640 A | 10/2007 |
| JP | 2009294338 A | 12/2009 |
| JP | 2010057316 A1 | 3/2010 |
| JP | 2010273417 A | 12/2010 |
| JP | 2012 192543 A | 10/2012 |
| JP | 2013162597 A1 | 8/2013 |
| JP | 2014223867 A | 12/2014 |
| KR | 2011/C89604 A | 3/2011 |

(56) References Cited

FOREIGN PATENT DOCUMENTS

| WO | 2006/124663 A2 | 11/2006 |
|---|---|---|
| WO | 2006-0127281 A1 | 11/2006 |
| WO | 2011/067646 A1 | 6/2011 |
| WO | 2011/126909 A2 | 10/2011 |
| WO | 2012/105448 A1 | 9/2012 |
| WO | 2013/015162 A1 | 1/2013 |
| WO | 2014103008 A1 | 7/2014 |
| WO | 2015/035406 A1 | 3/2015 |

OTHER PUBLICATIONS

U.S. Appl. No. 15/008,416, filed Jan. 27, 2016, Non-Final Office Action dated Jul. 6, 2016, all pages.
U.S. Appl. No. 15/006,126, filed Jan. 26, 2016, Non-Final Office Action dated Jul. 25, 2016, all pages.
U.S. Appl. No. 14/981,772, filed Dec. 28, 2015, Notice of Allowance dated Jul. 28, 2016, all pages.
U.S. Appl. No. 14/981,772, filed Dec. 28, 2015, Non-Final Office Action dated May 26, 2016, all pages.
U.S. Appl. No. 14/967,374, filed Dec. 14, 2015, Non-Final Office Action dated Jul. 13, 2016, all pages.
U.S. Appl. No. 14/967,373, filed Dec. 14, 2015, Final Office Action dated Sep. 2, 2016, all pages.
U.S. Appl. No. 14/967,373, filed Dec. 14, 2015, Non-Final Office Action dated Apr. 29, 2016, all pages.
U.S. Appl. No. 14/967,372, filed Dec. 14, 2015, Non-Final Office Action dated Jul. 15, 2016, all pages.
U.S. Appl. No. 14/967,371, filed Dec. 14, 2015, Notice of Allowance dated Aug. 29, 2016, all pages.
U.S. Appl. No. 14/967,371, filed Dec. 14, 2015, Non-Final Office Action dated May 3, 2016, all pages.
U.S. Appl. No. 14/967,370, filed Dec. 14, 2015, Notice of Allowance dated Aug. 30, 2016, all pages.
U.S. Appl. No. 14/967,370, filed Dec. 14, 2015, Non-Final Office Action dated Apr. 29, 2016, all pages.
U.S. Appl. No. 14/967,368, filed Dec. 14, 2015, Non-Final Office Action dated Apr. 22, 2016, all pages.
U.S. Appl. No. 14/967,366, filed Dec. 14, 2015, Final Office Action dated Aug. 31, 2016, all pages.
U.S. Appl. No. 14/967,366, filed Dec. 14, 2015, Non-Final Office Action dated Apr. 7, 2016, all pages.
U.S. Appl. No. 14/967,364, filed Dec. 14, 2015, Final Office Action dated Aug. 2, 2016, all pages.
U.S. Appl. No. 14/967,364, filed Dec. 14, 2015, Non-Final Office Action dated Mar. 7, 2016, all pages.
U.S. Appl. No. 14/967,360, Final Office Action dated Aug. 3, 2016, all pages.
U.S. Appl. No. 14/967,360, Non-Final Office Action dated Apr. 4, 2016, all pages.
U.S. Appl. No. 14/967,359, filed Dec. 14, 2015, Non-Final Office Action dated Apr. 1, 2016, all pages.
U.S. Appl. No. 14/967,357, filed Dec. 14, 2015, Final Office Action dated Sep. 29, 2016, all pages.
U.S. Appl. No. 14/967,357, filed Dec. 14, 2015, Non-Final Office Action dated Jun. 3, 2016, all pages.
U.S. Appl. No. 14/967,356, filed Dec. 14, 2015, Final Office Action dated Aug. 3, 2016, all pages.
U.S. Appl. No. 14/967,356, filed Dec. 14, 2015, Non-Final Office Action dated Apr. 15, 2016, all pages.
U.S. Appl. No. 14/883,621, filed Oct. 15, 2015, Notice of Allowance dated Sep. 14, 2016, all pages.
U.S. Appl. No. 14/883,621, filed Oct. 15, 2015, Non-Final Office Action dated Apr. 25, 2016, all pages.
U.S. Appl. No. 14/883,605, filed Oct. 14, 2015, Notice of Allowance dated Aug. 31, 2016, all pages.
U.S. Appl. No. 14/883,605, filed Oct. 14, 2015, Non-Final Office Action dated Apr. 14, 2016, all pages.
U.S. Appl. No. 14/883,599, filed Oct. 14, 2015, Non-Final Office Action dated Apr. 5, 2016, all pages.
U.S. Appl. No. 14/842,803, filed Sep. 1, 2015, Notice of Allowance dated Sep. 12, 2016, all pages.
U.S. Appl. No. 14/842,803, filed Sep. 1, 2015, Non-Final Office Action dated Apr. 29, 2016, all pages.
U.S. Appl. No. 14/821,789, filed Aug. 10, 2015, Non-Final Office Action dated Oct. 17, 2016, all pages.
U.S. Appl. No. 14/816,065, filed Aug. 3, 2015, Notice of Allowance dated Aug. 26, 2016, all pages.
U.S. Appl. No. 14/816,065, filed Aug. 3, 2015, Non-Final Office Action dated May 3, 2016, all pages.
U.S. Appl. No. 14/816,064, filed Aug. 3, 2015, Notice of Allowance dated Aug. 31, 2016, all pages.
U.S. Appl. No. 14/816,064, filed Aug. 3, 2015, Non-Final Office Action dated Apr. 29, 2016, all pages.
U.S. Appl. No. 14/748,210, filed Jun. 23, 2015, Notice of Allowance dated Jun. 3, 2016, all pages.
Niels Jegenhorst et al: : "Entwicklung eines Zellensensors fur Fahrzeugbatterien mit bidirektionaler drahtloser Kommunikation" Oct. 27, 2011 (Oct. 27, 2011), pp. 1-413, XP055296336, Hamburg, Retrieved from the Internet: URL:http://edoc.sub.uni-hamburg.de/hawjvol Itexte/2012/1535/pdf/Masterarbeit.pdf.
Shema Ann Mathew et al: "A smart wireless battery monitoring system for Electric Vehicles" Intelligent Systems Design and Applications (ISDA), 2012 12th International Conference on, IEEE, Nov. 27, 2012 (Nov. 27, 2012), pp. 189-193.
Matthias Schneider et al: "Automotive battery monitoring by wireless cell sensors", 2013 IEEE International Instrumentation and Measurement Technology Conference (12MTC) IEEE, May 13, 2012 (May 13, 2012), pp. 816-820.
Damian Alonso et al: "Towards a Wireless Battery Management System: Evaluation of Antennas and Radio Channel Measurements Inside a Battery Emulator", 2014 IEEE 80th Vehicular Technology Conference (VTC2014-Fall), Sep. 2014 (Sep. 2014), pp. 1-5.
Roscher Valentin et al: "Synchronisation using wireless trigger-broadcast for impedance spectroscopy of battery cells" 2015 IEEE Sensors Applications Symposium (SAS), IEEE, Apr. 13, 2015 (Apr. 13, 2015), pp. 1-6.
European Search Report dated Aug. 30, 2016 in European Patent Application No. 16160450.9, all pages.
European Search Report for EP 16160467 dated Jul. 22, 2016, all pages.
European Search Report for EP 16160441 dated Jul. 7, 2016, all pages.
European Search Report for EP 16160486 dated Jul. 6, 2016, all pages.
Specification for U.S. Appl. No. 62/133,991, filed Mar. 16, 2015, Inventor: Lai, et al., all pages.
Specification for U.S. Appl. No. 62/150,848, filed Apr. 22, 2015, Inventor: Lai, et al., all pages.
Office Action and Search Report for Chinese Appln No. 201610143527.9 dated Oct. 30, 2017, 16 pages.
European Search Report for EP 16 16 0353 dated Jul. 18, 2016, 8 pages.

* cited by examiner

US 10,173,687 B2

METHOD FOR RECOGNIZING VEHICLE DRIVER AND DETERMINING WHETHER DRIVER CAN START VEHICLE

CROSS-REFERENCE TO RELATED APPLICATIONS

The present application claims priority to U.S. Provisional Patent Application 62/272,706, filed Dec. 30, 3015, which claims priority to U.S. Provisional Patent Application No. 62/133,991, filed Mar. 16, 2015, and U.S. Provisional Patent Application No. 62/150,848, filed Apr. 22, 2015, the disclosures of which are hereby incorporated by reference in their entireties for all purposes.

BACKGROUND

The present disclosure relates to vehicle control technology, and more particularly to methods for increasing vehicle safety by analyzing a driver's physical condition.

A traditional vehicle is started by a matched key, which may be convenient in many circumstances. However, the traditional matched key approach is not particularly safe for at least two reasons. First, anyone who has the key of the vehicle can start the vehicle, which may incentivize theft. Second, drivers whose physical condition are not suitable for driving, due to intoxication, likeliness of a heart attack, etc., are allowed to start the vehicle without any prohibitive measures. Current vehicle technologies do not address these safety concerns.

SUMMARY

Provided is a method for determining whether a driver can operate a vehicle. The method may include determining, at a processor within the vehicle, whether a physical status of the driver is acceptable using a first set of sensors. The physical status of the driver may be acceptable when the first set of sensors indicate that the driver has a capacity to operate the vehicle. The first set of sensors may include one of several components. The first set of sensors may include an electrocardiogram detection component configured to detect a cardiac activity of the driver. The first set of sensors may also include an alcohol detection component configured to detect a breathing gas of the driver. In addition, the first set of sensors may include a body temperature detection component configured to detect a body temperature of the driver. Furthermore, the first set of sensors may include a photography component configured to detect an eye expression of the driver;

In some embodiments, the method may include determining, at the processor within the vehicle, whether the identity of the driver is acceptable using a second set of sensors. The identity of the driver is acceptable when the second set of sensors indicate that the driver is an authorized driver. The second set of sensors may include one of several components. The second set of sensors may include a fingerprint detection component configured to detect a fingerprint of the driver. The second set of sensors may also include the electrocardiogram detection component configured to detect the cardiac activity of the driver. Furthermore, the second set of sensors may include the photography component configured to detect an image of the driver. The method may also include determining whether the driver can operate the vehicle based on whether both the physical status of the driver and the identity of the driver are acceptable.

In some embodiments, the physical status of the driver is determined to be unacceptable when the electrocardiogram detection component detects that the cardiac activity of the driver indicates that the likelihood of cardiac arrest of the driver exceeds a certain threshold. In some embodiments, the electrocardiogram signal may be extracted from the cardiac activity of the driver, and the P wave, Q wave, R wave, S wave, and T wave may be extracted from the electrocardiogram signal. In some embodiments, the physical status of the driver is determined to be unacceptable when the alcohol detection component detects that the breathing gas of the driver indicates that the blood alcohol content of the driver exceeds a certain threshold.

In some embodiments, the physical status of the driver is determined to be unacceptable when the body temperature detection component detects that the body temperature of the driver is above or below certain thresholds. In some embodiments, the physical status of the driver is determined to be unacceptable when the photography component detects that the eye expression of the driver indicates that the likelihood of drowsiness exceeds a certain threshold. In some embodiments, the identity of the driver is determined to be acceptable when the fingerprint detection component detects that the fingerprint of the driver matches a fingerprint stored in a server of acceptable driver fingerprints.

In some embodiments, the identity of the driver is determined to be acceptable when the electrocardiogram detection component detects that the cardiac activity of the driver matches a cardiac activity stored in a server of acceptable driver cardiac activities. In some embodiments, the method may also include activating, at a processor within the vehicle, an alarm system when it is determined that the identity of the driver is unacceptable. Furthermore, the method may include activating, at the processor within the vehicle, an automatic driving system when it is determined that the physical status of the driver is unacceptable. Also provided in the present disclosure are systems that implement the described method.

BRIEF DESCRIPTION OF THE DRAWINGS

The accompanying drawings, which are included to provide a further understanding of the invention, are incorporated in and constitute a part of this specification, illustrate embodiments of the invention and together with the detailed description serve to explain the principles of the invention. No attempt is made to show structural details of the invention in more detail than may be necessary for a fundamental understanding of the invention and various ways in which it may be practiced.

In the appended figures, similar components and/or features may have the same numerical reference label. Further, various components of the same type may be distinguished by following the reference label by a letter that distinguishes among the similar components and/or features. If only the first numerical reference label is used in the specification, the description is applicable to any one of the similar components and/or features having the same first numerical reference label irrespective of the letter suffix.

DETAILED DESCRIPTION OF THE INVENTION

Various specific embodiments of the present disclosure will be described below with reference to the accompanying drawings constituting a part of this specification. It should be understood that, although structural parts and components of various examples of the present disclosure are described by using terms expressing directions, e.g., "front", "back", "upper", "lower", "left", "right" and the like in the present disclosure, these terms are merely used for the purpose of convenient description and are determined on the basis of exemplary directions displayed in the accompanying drawings. Since the embodiments disclosed by the present disclosure may be set according to different directions, these terms expressing directions are merely used for describing rather than limiting. Under possible conditions, identical or similar reference numbers used in the present disclosure indicate identical components.

The present disclosure relates to systems and methods for increasing vehicle safety by recognizing the identity of a vehicle driver, determining the physical status of the driver, and determining whether it is safe for the driver to start a vehicle based on the driver's identity and the driver's physical status.

Figure 1:
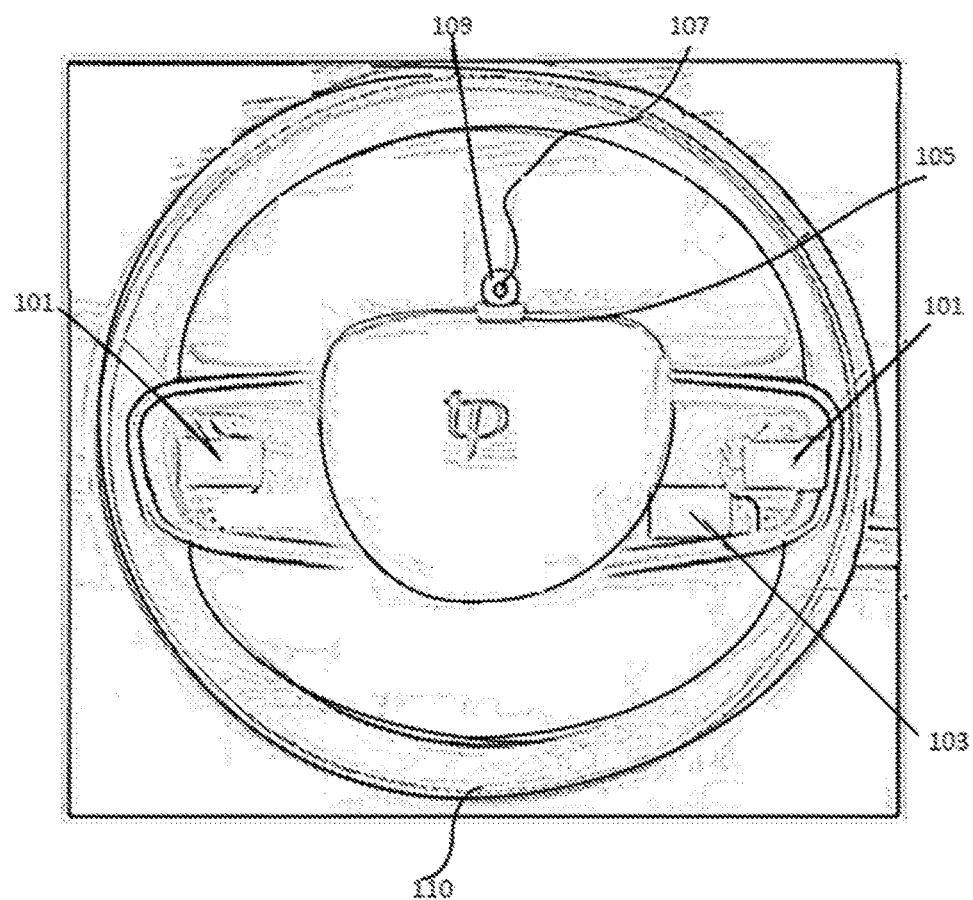
FIG. 1 shows a schematic diagram of a driver physiological characteristic detection system on a steering wheel of a vehicle, according to an exemplary embodiment of the present disclosure.

FIG. 1 shows a schematic diagram of a driver physiological characteristic detection system 100, according to an exemplary embodiment of the present disclosure. In some embodiments, the driver physiological characteristic detection system 100 comprises a plurality of detection devices (sensors) arranged at different positions on a steering wheel 110 of the vehicle. In other embodiments, the detection devices may be arranged at various locations throughout the vehicle cabin other than the steering wheel. The detection devices may include electrocardiogram detection devices 101 arranged on the left side and the right side of the steering wheel 110, a fingerprint detection device 103, an alcohol detection device 105, a body temperature detection device 107 in the middle of the steering wheel 110, and a photography analysis device 109 in the middle of the steering wheel 110.

The electrocardiogram detection devices 101 are used for detecting the cardiac activity of the driver when the driver's hands are laid on the two sides of the steering wheel 110. The signal of interest for the electrocardiogram detection devices 101 is an electrocardiogram signal. The electrocardiogram signal may be further analyzed to extract different characteristics of the signal, including P, Q, R, S and T waves which are commonly extracted from electrocardiogram signals.

The fingerprint detection device 103 is used for detecting the fingerprints of the driver to generate a fingerprint signal. The signal of interest for the fingerprint detection device 103 is a fingerprint image of the driver, which may be captured through any one of a wide number of available fingerprint scanning technologies. For example, fingerprint detection device 103 may be a an optical sensor, a capacitive sensor, an ultrasound sensor, or a thermal sensor, among others. In some embodiments, fingerprint detection device 103 may be a capacitive sensor that determines each pixel value of an image based on the capacitance measured at each pixel location, which varies due to the different dielectric constants of skin ridges compared to a valleys. In some embodiments, fingerprint detection device 103 may employ a high frequency ultrasound or optical sensor that receives a varying signal based on the change in light reflectance related to the skin ridges. In some embodiments, fingerprint detection device 103 is a thermal scanner that measures the difference in temperature of different pixel areas, with high temperature areas corresponding to skin ridges and low temperature areas corresponding to valleys.

In some embodiments, the signal that is captured by fingerprint detection device 103 may be an image file. The image file may be compressed or uncompressed, and may be any one of several digital image file types, such as TIFF, JPEG, GIF, PNG, BMP, etc. In some embodiments, the image file may not be a traditional image file type, but may be a data representation of fingerprint topography. For example, while a fingerprint usually appears as a series of dark lines that represent ridges of the skin, the image file may be an integer representing the number of ridges of the skin. Furthermore, the image file may be an integer representing the number of crossovers, ridge bifurcations, ridge endings, islands, or pores. Furthermore, the image file may be any digital representation of any feature of a fingerprint.

The alcohol detection device 105 may be used for detecting the breathing gas of the driver to estimate the driver's blood alcohol content (BAC). In some embodiments, the breathing gas alcohol concentration signal of the driver may be used to yield an estimate of the driver's BAC. In some embodiments, the alcohol detection device 105 may be a breathalyzer in which the driver may breathe directly into to yield a BAC estimate.

The body temperature detection device 107 is used for detecting the body temperature of the driver to generate a body temperature signal of the driver. The photography analysis device 109 is used for detecting the eye expression of the driver to generate a sleepiness eye expression signal of the driver.

Figure 2:
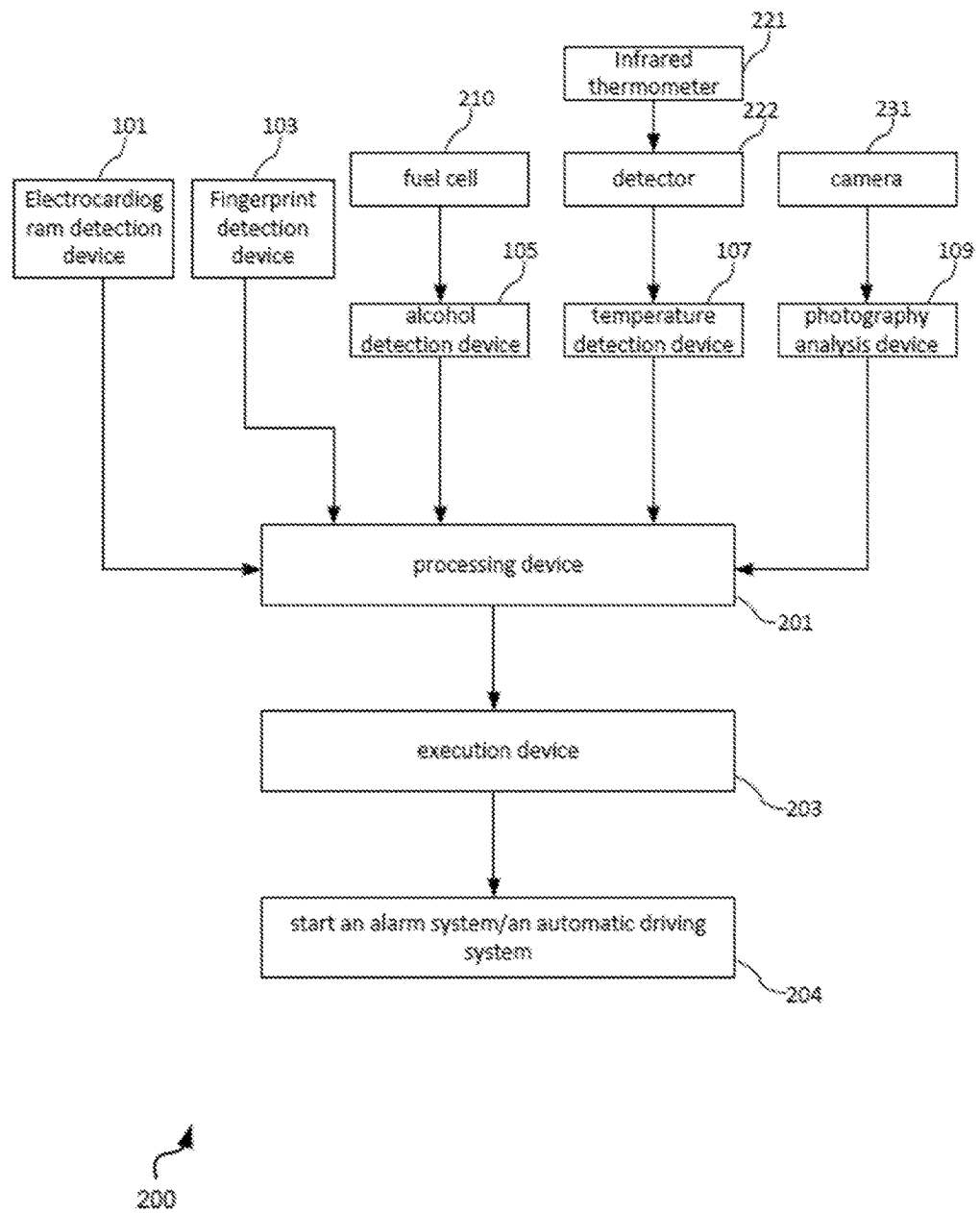
FIG. 2 shows a structural diagram of circuit modules of a driver physiological characteristic detection system, according to an exemplary embodiment of the present disclosure.

FIG. 2 shows a structural diagram of circuit modules of a driver physiological characteristic detection system 200. The driver physiological characteristic detection system 200 comprises the electrocardiogram detection devices 101, the fingerprint detection device 103, the alcohol detection device 105, the body temperature detection device 107, the photography analysis device 109, a processing device 201 and an execution device 203.

In some embodiments, the processing device 201 is connected with the electrocardiogram detection devices 101, the fingerprint detection device 103, the alcohol detection device 105, the body temperature detection device 107 and the photography analysis device 109, and receives sensor signals sent by them. The processing device 201 may also be connected with the execution device 203. In some embodiments, the processing device 201 may send a processing signal after analyzing the sensor signals to the execution device 203 for executing. The execution device 203 may start an alarm system, an automatic driving system, or initiates other safety protocols at block 204.

A fuel cell 210 may be arranged in or with the alcohol detection device 105. In some embodiments, the fuel cell 210 can convert alcohol in the breathing gas of the driver into an electrical signal of which the quantity of electricity is directly proportional to the alcohol content to determine the degree of intoxication of the driver. In some embodiments, an infrared thermometer 221 and a detector 222 are arranged in or with the body temperature detection device 107. In some embodiments, the infrared thermometer 221 collects human infrared energy and gathers the infrared energy in the detector 222. The detector 222 may then convert the infrared energy into an electrical signal. In some embodiments, a camera 231 is arranged in or with the photography analysis device 109, the camera 231 picks up mental and physical status information such as eyeball position and viewing condition of the driver. The photography analysis device 109 may determine whether the mental status of the driver is good according to the mental status information.

Figure 3:
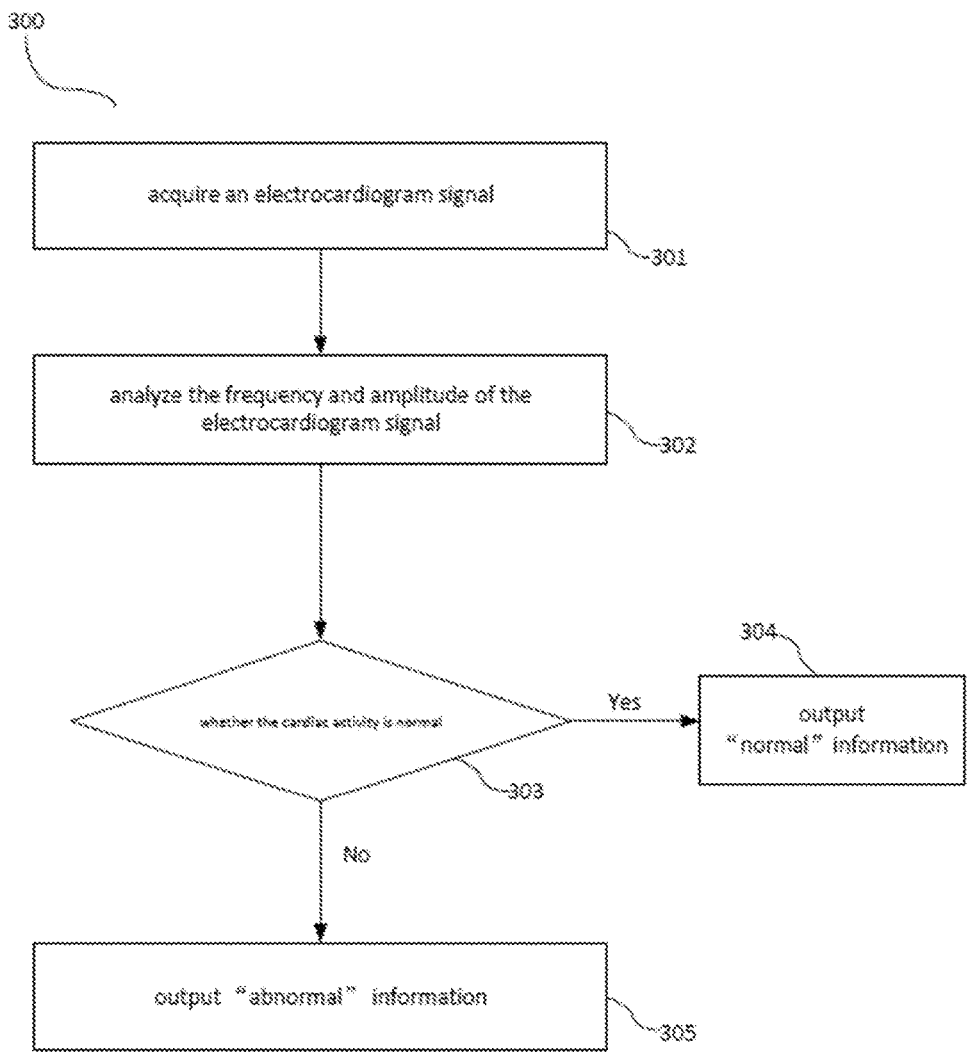
FIG. 3 shows a schematic flowchart of an electrocardiogram analysis, according to an exemplary embodiment of the present disclosure.

FIG. 3 shows a schematic flowchart of an electrocardiogram analysis 300, according to an exemplary embodiment of the present disclosure. As shown in FIG. 3, after the driver enters the cabin of the vehicle, an electrocardiogram signal is acquired at step 301. In some embodiments, this step occurs while both hands of the driver are on the two sides of the steering wheel 110. In some embodiments, the electrocardiogram detection devices 101 detect the change in cardiac activity of the driver to generate an electrocardiogram signal. Each electrocardiogram detection device 101 may include a touchpad, an analysis system, and a microelectrode (sensor) that is arranged on the touchpad. During cardiac activity, ions may enter into and exit from the cardiac muscles (cells) which produce an electric potential difference. When the fingers of both hands of the driver touch the microelectrodes of the electrocardiogram detection devices 101, the electric potential difference inside and outside the cardiac muscle cells change due to the change of cardiac activity. The tiny electrical pulse is recorded using the microelectrodes, and the signal represented after the electric potential difference is filtered and amplified is an electrocardiogram.

At step 302, characteristics such as frequency and amplitude in the electrocardiogram signal are analyzed. At step 303, the electrocardiogram detection devices 101 determine whether the cardiac activity is normal according to the analysis result. If it is determined to be normal, step 304 is executed, otherwise step 305 is executed. At step 304, the electrocardiogram detection devices 101 send a "normal" cardiac signal to the processing device 201 at the moment the cardiac status of the driver is determined to be favorable for safely driving the vehicle. At step 305, the electrocardiogram detection devices 101 send an "abnormal" cardiac signal to the processing device 201 at the moment the cardiac status of the driver is determined to be unfavorable for safely driving the vehicle. When step 305 is performed, the processing device 201 starts the alarm system, the automatic driving system, or initiates other safety protocols at block 204.

Figure 4:
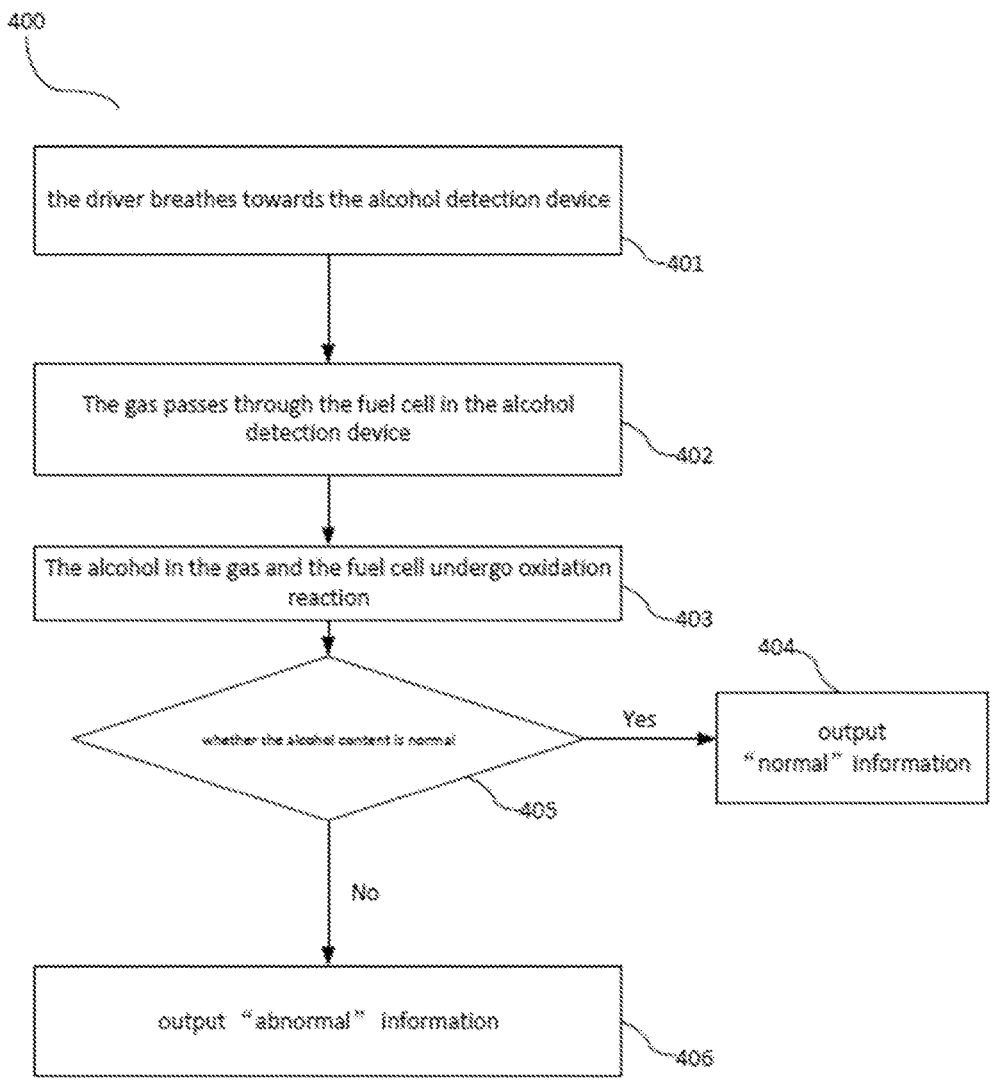
FIG. 4 shows a schematic flowchart of a respiration analysis, according to an exemplary embodiment of the present disclosure.

FIG. 4 shows a schematic flowchart of a respiration analysis 400, according to an exemplary embodiment of the present disclosure. As shown in FIG. 4, after the driver enters the cabin of the vehicle, the driver may breathe towards the alcohol detection device 105 at step 401. At step 402, the gas from the driver's breathing may pass through the fuel cell 210 in the alcohol detection device 105. At step 403, if the gas has alcohol, the alcohol may be oxidized in the fuel cell 210. In some embodiments, the breathing gas alcohol concentration is measured according to the following principle. Because the alcohol in blood may be freely diffused into the lung, Henry's Law indicates that the solubility of the gas in liquid is directly proportional to the partial pressure of the gas in a gaseous phase, thus, the ratio of the BAC to the gas alcohol concentration breathed by the lung is definite at a fixed temperature under fixed pressure. Presently, the accepted ratio of the BAC to the breathing alcohol concentration (BrAC) is 2100:1, i.e., the alcohol content in 2100 milliliters of breathing gas is approximately equal to that in 1 milliliter of blood. In some embodiments, when the gas breathed by the driver contains alcohol, the electrochemical reaction of the alcohol and the fuel cell may be determined according to the following equation:

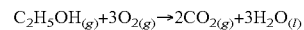

$$C_2H_5OH_{(g)} + 3O_{2(g)} \rightarrow 2CO_{2(g)} + 3H_2O_{(l)}$$

That is, the chemical energy can be converted into electrical energy. When the driver blows into the alcohol detection device, a fuel is provided to the fuel cell. The higher the blood alcohol concentration is, the higher the partial pressure of the alcohol in the breathing gas is, which causes the reaction to work rightward according to Le Chatelier's principle, which creates a higher voltage in the fuel cell.

At step 404, the current directly proportional to the alcohol content is generated in the oxidization reaction. At step 405, the alcohol detection device 105 determines whether the alcohol content is normal according to the magnitude of the generated current. If it is determined to be normal, step 406 is executed, otherwise step 407 is executed. At step 406, the alcohol detection device 105 sends a "normal" alcohol content signal to the processing device 201 at the moment it is determined that the driver has not been drinking or the alcohol content is low and does not influence safe driving. At step 407, the alcohol detection device 105 sends an "abnormal" alcohol content signal to the processing device 201 at the moment it is determined that the alcohol content of the driver is high and influences safe driving. When step 407 is performed, the processing device 201 starts the alarm system, the automatic driving system, or initiates other safety protocols at block 204.

Figure 5:
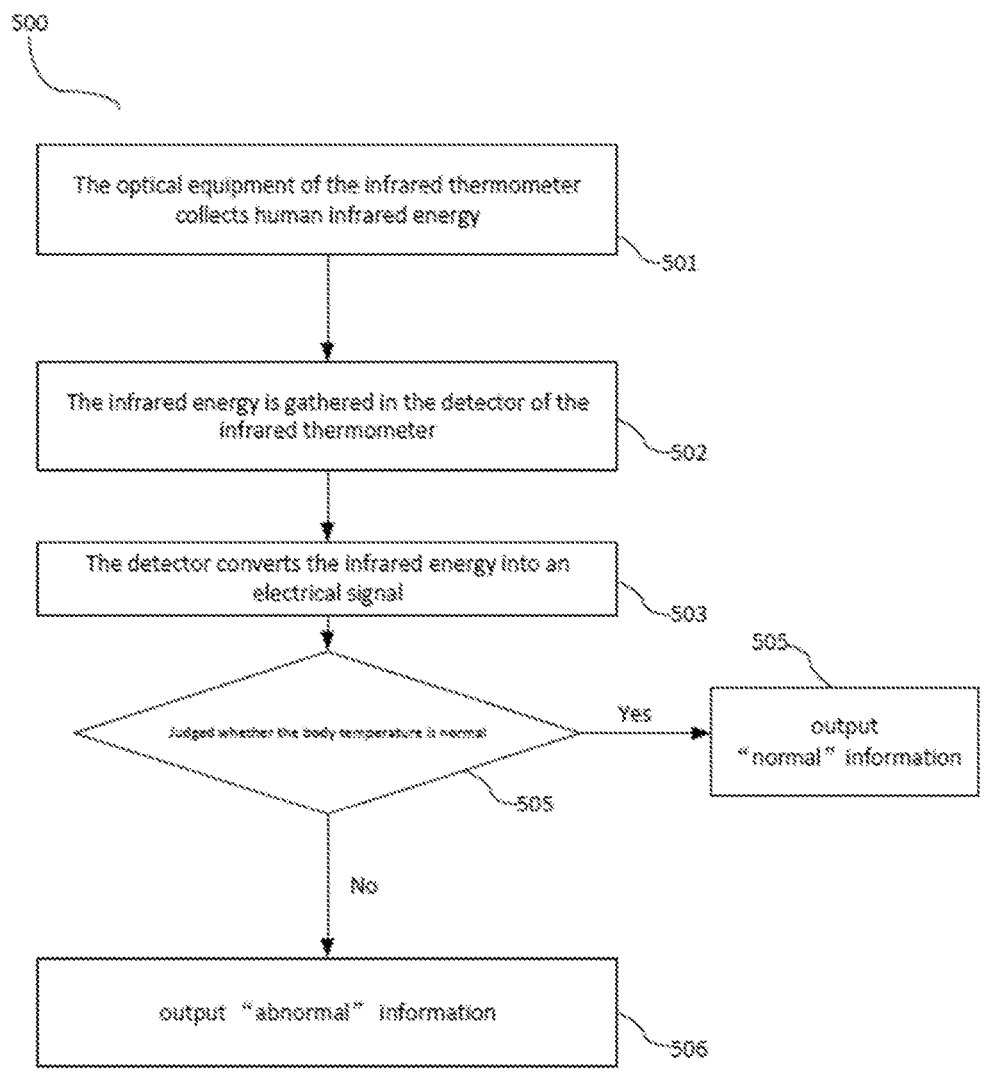
FIG. 5 shows a schematic flowchart of a body temperature analysis, according to an exemplary embodiment of the present disclosure.

FIG. 5 shows a schematic flowchart of a body temperature analysis 500, according to an exemplary embodiment of the present disclosure. As shown in FIG. 5, after the driver enters the cabin of the vehicle, the infrared thermometer 221 of the body temperature detection device 107 collects human infrared energy at step 501. At step 502, the infrared energy is gathered in the detector 222. At step 503, the detector 222 converts the infrared energy into an electrical signal.

At step 504, the body temperature detection device 107 determines whether the body temperature of the driver is normal according to the electrical signal. If it is determined to be normal, step 505 is executed, otherwise step 506 is executed. At step 505, the body temperature detection device 107 sends a "normal" body temperature signal to the processing device 201 at the moment it is determined that the body temperature of the driver is normal and does not influence safe driving. At step 506, the body temperature detection device 107 sends an "abnormal" body temperature signal to the processing device 201 at the moment it is determined that the body temperature of the driver is abnormal and may influence safe driving. When step 506 is performed, the processing device 201 starts the alarm system, the automatic driving system, or initiates other safety protocols at block 204.

Figure 6:
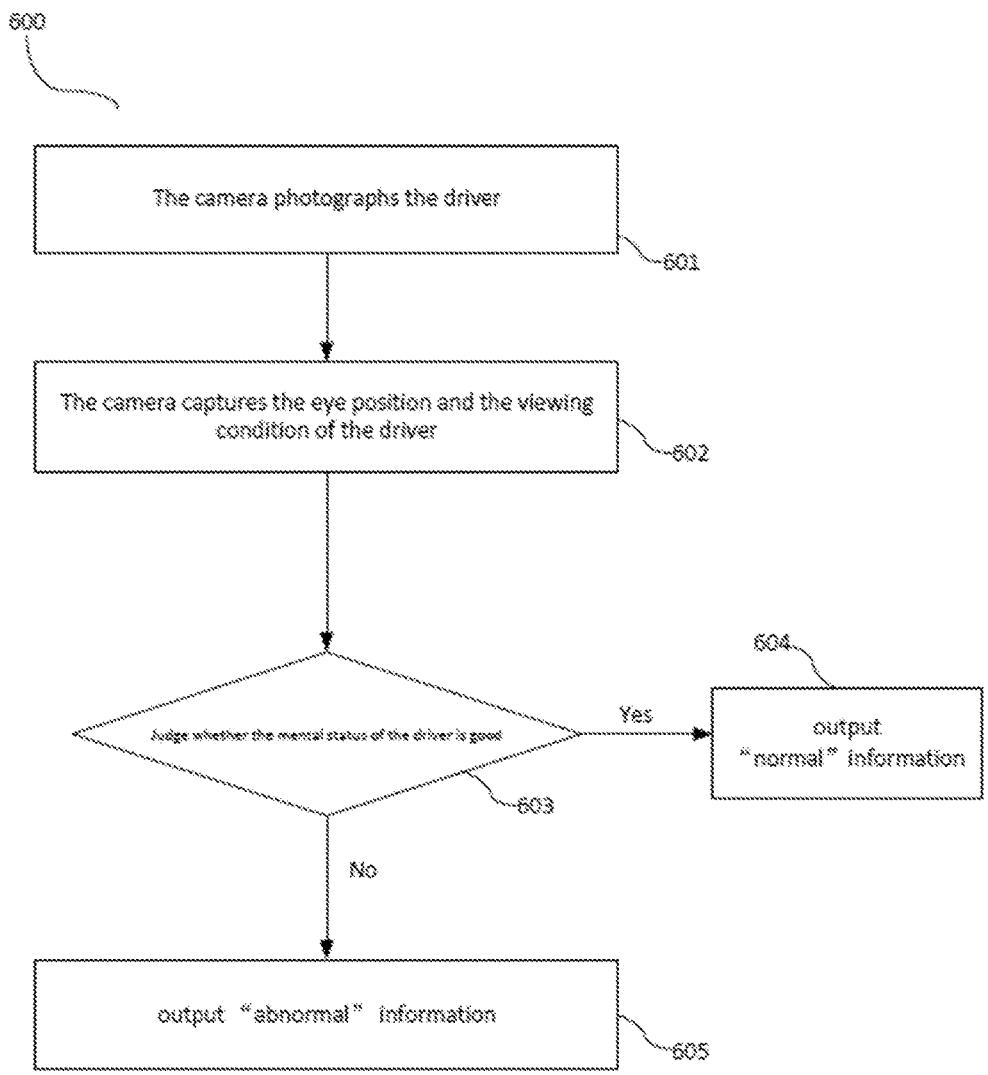
FIG. 6 shows a schematic flowchart of a sleepiness eye expression analysis, according to an exemplary embodiment of the present disclosure.

FIG. 6 shows a schematic flowchart of a sleepiness eye expression analysis 600, according to an exemplary embodiment of the present disclosure. As shown in FIG. 6, after the driver enters the cabin of the vehicle, the camera 231 photographs the driver at step 601. At step 602, the camera 231 captures mental status information such as eyeball position and viewing condition of the driver. At step 603, the photography analysis device 109 determines whether the mental status of the driver is good according to the mental status information. If it is determined to be good, step 604 is executed, otherwise step 605 is executed. At step 604, the photography analysis device 109 sends a "normal" driver's mental status signal to the processing device 201 at the moment it is determined that the mental status of the driver does not influence safe driving. At step 605, the photography analysis device 109 sends an "abnormal" driver's mental status signal to the processing device 201 at the moment it is determined that the mental status of the driver may influence safe driving. When step 605 is performed, the processing device 201 starts the alarm system, the automatic driving system, or initiates other safety protocols at block 204.

Figure 7:
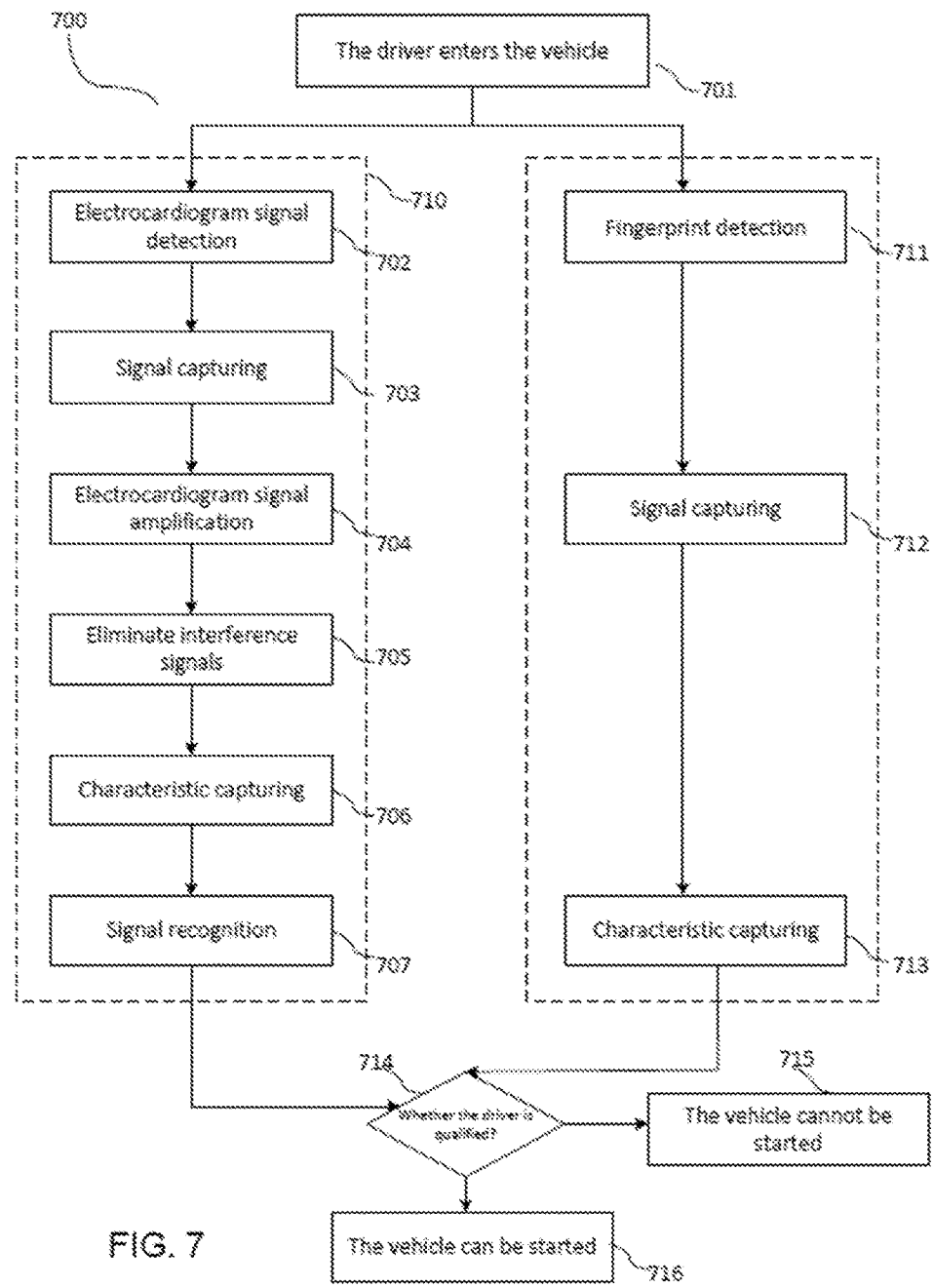
FIG. 7 shows a schematic flowchart of a driver physiological characteristic detection analysis, according to an exemplary embodiment of the present disclosure.

FIG. 7 shows a schematic flowchart of a driver physiological characteristic detection analysis 700, according to an exemplary embodiment of the present disclosure. As shown in FIG. 7, the driver enters the cab of the vehicle at step 701. The driver physiological characteristic detection analysis 700 then splits into two branches. The first branch 710 deals with determining the physical status of the driver, and in some embodiments is an electrocardiogram detection including steps 702 through 707, as shown in FIG. 7. The second branch 720 deals with recognizing the identity of the driver, and in some embodiments is a fingerprint detection including steps 711 through 713, as shown in FIG. 7. In some embodiments, the first and second branches 710 and 720 are initiated simultaneously. In some embodiments, the first and second branches 710 and 720 are initiated sequentially.

Referring now to the first branch 710, the electrocardiogram detection devices 101 are started at step 702. At step 703, the electrocardiogram detection devices 101 capture electrocardiogram signals of the driver. At step 704, the electrocardiogram signals are amplified. At step 705, interference signals are eliminated. At step 706, characteristic signals are captured and waveform characteristics of waves P, Q, R, S and T in the electrocardiogram signals are extracted. At step 707, the electrocardiogram detection devices 101 analyze and compare these characteristic signals with characteristic signals stored in a database of a memory (the memory is the prior art, and therefore is omitted in the figures) and send the comparison information to the processing device 201 for determining whether the driver is qualified.

Referring now to the second branch 720, the fingerprint detection device 103 is started at step 711. At step 712, the fingerprint detection device 103 scans and captures fingerprint signals of the driver. At step 713, the fingerprint detection device 103 captures characteristic signals in the fingerprint signals, compares the characteristic signals with fingerprint information in the database, and sends the comparison information to the processing device 201 for determining whether the identity of the driver is qualified. At step 714, the processing device 201 receives the information of the electrocardiogram detection devices 101 and the fingerprint detection device 103. When the two pieces of information simultaneously affirm that the driver is qualified, step 716 is executed, otherwise step 715 is executed. At step 715, the vehicle cannot be started, and at step 716, the vehicle can be started.

In some embodiments, the first branch 710 and the second branch 720 may both deal with recognizing the identity of the driver, or may both deal with determining the physical status of the driver. When both branches deal with recognizing the identity of the driver, step 714 may consist of comparing the identity information from the electrocardiogram detection devices 101 and the fingerprint detection device 103. When the two pieces of information simultaneously affirm that the identity of the driver is qualified, step 716 is executed, otherwise step 715 is executed.

Figure 8:
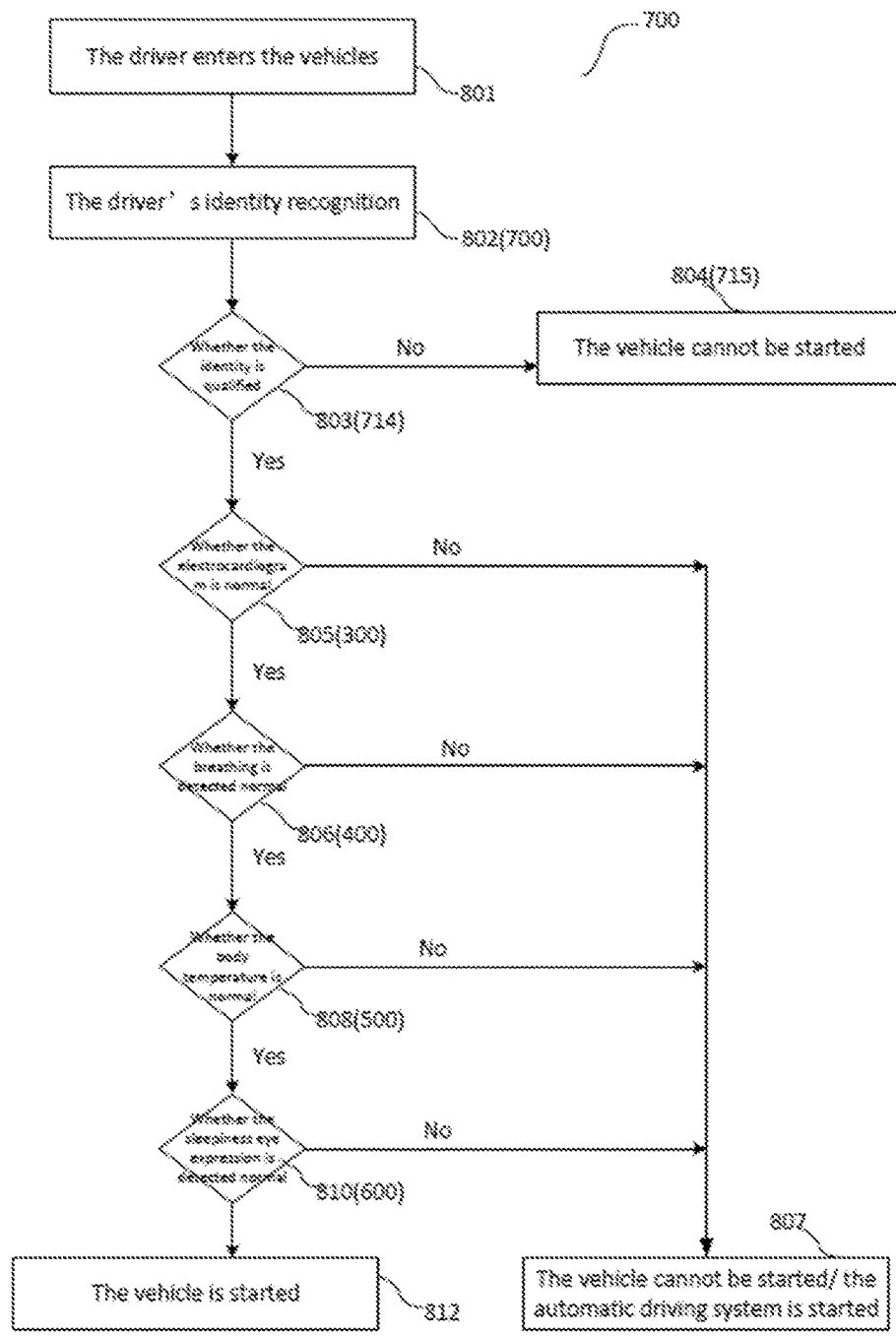
FIG. 8 shows a schematic flowchart of a driver physiological characteristic detection analysis, according to an exemplary embodiment of the present disclosure.

FIG. 8 shows a schematic flowchart of a driver physiological characteristic detection analysis 800, according to an exemplary embodiment of the present disclosure. As previously described, the present disclosure not only can determine whether the identity of the driver is qualified, but also determine whether the physical status of the driver is suitable for starting or continuing driving the vehicle through a number of different methods. At step 801, the driver enters the cab of the vehicle. At step 802, the driver's identity recognition is started, i.e., the flow 700 of recognition as shown in FIG. 7 may be started where both branches deal with recognizing the identity of the driver. At step 803, whether the identity of the driver is qualified is determined. If it is determined to be qualified, step 805 is executed, otherwise, step 804 is executed. At step 804, the vehicle cannot be started. At step 805, the flow 300 of the electrocardiogram determination shown in FIG. 3 is performed. If the cardiac activity of the driver is normal, step 806 is executed, and if the cardiac activity of the driver is abnormal, step 807 is executed.

At step 806, the flow 400 of the breathing detection shown in FIG. 4 is performed. If the alcohol content of the driver is normal, step 808 is executed. If the alcohol content of the driver is abnormal, step 807 is executed. At step 808, the flow 500 of the temperature detection shown in FIG. 5 is performed. If the body temperature of the driver is normal, step 810 is executed. If the body temperature of the driver is abnormal, step 807 is executed. At step 810, the flow 600 of the sleepiness eye expression detection shown in FIG. 6 is performed. If the mental status of the driver is normal, step 812 is executed. If the mental status of the driver is abnormal, step 807 is executed. At step 812, the driver is allowed to start the vehicle. At step 807, the execution device 203 is started, i.e., the alarm system or the automatic driving system is started.

Moreover, in some embodiments, when the automatic driving system of the vehicle is started, the automatic driving system may carry the driver to the designated place, e.g., a residence or a hospital, according to the determination results of steps 805-810. For example, when the electrocardiogram determination of the driver is abnormal, the driver can be automatically carried to the hospital. The hospital may be a hospital closest to the accident place or a fixed hospital. During a first driving, the hospital may be set in a system of a console, and may also be modified later. When the breathing, the body temperature or the sleepiness of the driver is detected to be abnormal, the driver can be automatically carried to home. The address of the home may also be set in the system of the console, and may also be modified later.

Figure 9:
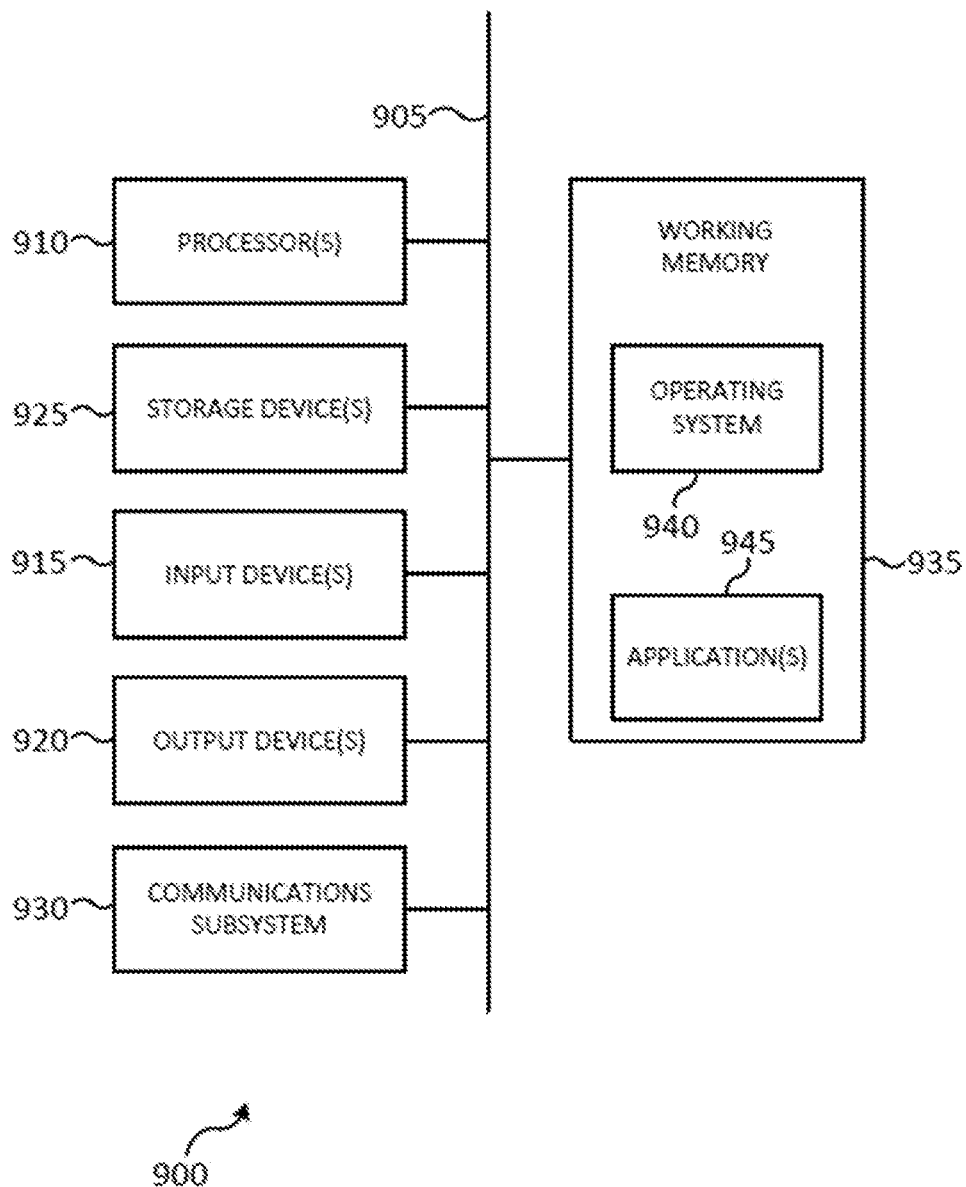
FIG. 9 illustrates a simplified computer system, according to an exemplary embodiment of the present disclosure.

FIG. 9 illustrates a simplified computer system, according to an exemplary embodiment of the present disclosure. A computer system 900 as illustrated in FIG. 9 may be incorporated into devices such as a portable electronic device, mobile phone, or other device as described herein. FIG. 9 provides a schematic illustration of one embodiment of a computer system 900 that can perform some or all of the steps of the methods provided by various embodiments. It should be noted that FIG. 9 is meant only to provide a generalized illustration of various components, any or all of which may be utilized as appropriate. FIG. 9, therefore, broadly illustrates how individual system elements may be implemented in a relatively separated or relatively more integrated manner.

The computer system 900 is shown comprising hardware elements that can be electrically coupled via a bus 905, or may otherwise be in communication, as appropriate. The hardware elements may include one or more processors 910, including without limitation one or more general-purpose processors and/or one or more special-purpose processors such as digital signal processing chips, graphics acceleration processors, and/or the like; one or more input devices 915, which can include without limitation a mouse, a keyboard, a camera, and/or the like; and one or more output devices 920, which can include without limitation a display device, a printer, and/or the like.

The computer system 900 may further include and/or be in communication with one or more non-transitory storage devices 925, which can comprise, without limitation, local and/or network accessible storage, and/or can include, without limitation, a disk drive, a drive array, an optical storage device, a solid-state storage device, such as a random access memory ("RAM"), and/or a read-only memory ("ROM"), which can be programmable, flash-updateable, and/or the like. Such storage devices may be configured to implement any appropriate data stores, including without limitation, various file systems, database structures, and/or the like.

The computer system 900 might also include a communications subsystem 930, which can include without limitation a modem, a network card (wireless or wired), an infrared communication device, a wireless communication device, and/or a chipset such as a Bluetooth™ device, an 802.11 device, a WiFi device, a WiMax device, cellular communication facilities, etc., and/or the like. The communications subsystem 930 may include one or more input and/or output communication interfaces to permit data to be exchanged with a network such as the network described below to name one example, other computer systems, television, and/or any other devices described herein. Depending on the desired functionality and/or other implementation concerns, a portable electronic device or similar device may communicate image and/or other information via the communications subsystem 930. In other embodiments, a portable electronic device, e.g. the first electronic device, may be incorporated into the computer system 900, e.g., an electronic device as an input device 915. In some embodiments, the computer system 900 will further comprise a working memory 935, which can include a RAM or ROM device, as described above.

The computer system 900 also can include software elements, shown as being currently located within the working memory 935, including an operating system 940, device drivers, executable libraries, and/or other code, such as one or more application programs 945, which may comprise computer programs provided by various embodiments, and/or may be designed to implement methods, and/or configure systems, provided by other embodiments, as described herein. Merely by way of example, one or more procedures described with respect to the methods discussed above, such as those described in relation to FIG. 9, might be implemented as code and/or instructions executable by a computer and/or a processor within a computer; in an aspect, then, such code and/or instructions can be used to configure and/or adapt a general purpose computer or other device to perform one or more operations in accordance with the described methods.

A set of these instructions and/or code may be stored on a non-transitory computer-readable storage medium, such as the storage device(s) 925 described above. In some cases, the storage medium might be incorporated within a computer system, such as computer system 900. In other embodiments, the storage medium might be separate from a computer system e.g., a removable medium, such as a compact disc, and/or provided in an installation package, such that the storage medium can be used to program, configure, and/or adapt a general purpose computer with the instructions/code stored thereon. These instructions might take the form of executable code, which is executable by the computer system 900 and/or might take the form of source and/or installable code, which, upon compilation and/or installation on the computer system 900 e.g., using any of a variety of generally available compilers, installation programs, compression/decompression utilities, etc., then takes the form of executable code.

It will be apparent to those skilled in the art that substantial variations may be made in accordance with specific requirements. For example, customized hardware might also be used, and/or particular elements might be implemented in hardware, software including portable software, such as applets, etc., or both. Further, connection to other computing devices such as network input/output devices may be employed.

As mentioned above, in one aspect, some embodiments may employ a computer system such as the computer system 900 to perform methods in accordance with various embodiments of the technology. According to a set of embodiments, some or all of the procedures of such methods are performed by the computer system 900 in response to processor 910 executing one or more sequences of one or more instructions, which might be incorporated into the operating system 940 and/or other code, such as an application program 945, contained in the working memory 935. Such instructions may be read into the working memory 935 from another computer-readable medium, such as one or more of the storage device(s) 925. Merely by way of example, execution of the sequences of instructions contained in the working memory 935 might cause the processor(s) 910 to perform one or more procedures of the methods described herein. Additionally or alternatively, portions of the methods described herein may be executed through specialized hardware.

The terms "machine-readable medium" and "computer-readable medium," as used herein, refer to any medium that participates in providing data that causes a machine to operate in a specific fashion. In an embodiment implemented using the computer system 900, various computer-readable media might be involved in providing instructions/code to processor(s) 910 for execution and/or might be used to store and/or carry such instructions/code. In many implementations, a computer-readable medium is a physical and/or tangible storage medium. Such a medium may take the form of a non-volatile media or volatile media. Non-volatile media include, for example, optical and/or magnetic disks, such as the storage device(s) 925. Volatile media include, without limitation, dynamic memory, such as the working memory 935.

Common forms of physical and/or tangible computer-readable media include, for example, a floppy disk, a flexible disk, hard disk, magnetic tape, or any other magnetic medium, a CD-ROM, any other optical medium, punchcards, papertape, any other physical medium with patterns of holes, a RAM, a PROM, EPROM, a FLASH-EPROM, any other memory chip or cartridge, or any other medium from which a computer can read instructions and/or code.

Various forms of computer-readable media may be involved in carrying one or more sequences of one or more instructions to the processor(s) 910 for execution. Merely by way of example, the instructions may initially be carried on a magnetic disk and/or optical disc of a remote computer. A remote computer might load the instructions into its dynamic memory and send the instructions as signals over a transmission medium to be received and/or executed by the computer system 900.

The communications subsystem 930 and/or components thereof generally will receive signals, and the bus 905 then might carry the signals and/or the data, instructions, etc. carried by the signals to the working memory 935, from which the processor(s) 910 retrieves and executes the instructions. The instructions received by the working memory 935 may optionally be stored on a non-transitory storage device 925 either before or after execution by the processor(s) 910.

The methods, systems, and devices discussed above are examples. Various configurations may omit, substitute, or add various procedures or components as appropriate. For instance, in alternative configurations, the methods may be performed in an order different from that described, and/or various stages may be added, omitted, and/or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Specific details are given in the description to provide a thorough understanding of exemplary configurations including implementations. However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure.

Also, configurations may be described as a process which is depicted as a schematic flowchart or block diagram. Although each may describe the operations as a sequential process, many of the operations can be performed in parallel or concurrently. In addition, the order of the operations may be rearranged. A process may have additional steps not included in the figure. Furthermore, examples of the methods may be implemented by hardware, software, firmware, middleware, microcode, hardware description languages, or any combination thereof. When implemented in software, firmware, middleware, or microcode, the program code or code segments to perform the necessary tasks may be stored in a non-transitory computer-readable medium such as a storage medium. Processors may perform the described tasks.

Having described several example configurations, various modifications, alternative constructions, and equivalents may be used without departing from the spirit of the disclosure. For example, the above elements may be components of a larger system, wherein other rules may take precedence over or otherwise modify the application of the technology. Also, a number of steps may be undertaken before, during, or after the above elements are considered. Accordingly, the above description does not bind the scope of the claims.

As used herein and in the appended claims, the singular forms "a", "an", and "the" include plural references unless the context clearly dictates otherwise. Thus, for example, reference to "a user" includes a plurality of such users, and reference to "the processor" includes reference to one or more processors and equivalents thereof known to those skilled in the art, and so forth.

Also, the words "comprise", "comprising", "contains", "containing", "include", "including", and "includes", when used in this specification and in the following claims, are intended to specify the presence of stated features, integers, components, or steps, but they do not preclude the presence or addition of one or more other features, integers, components, steps, acts, or groups.

What is claimed is:

1. A method for determining whether a driver is permitted to start a vehicle, the method comprising:
   determining, at a processor within the vehicle, determining whether a physical status of the driver is acceptable using a first set of sensors, wherein determining whether the physical status of the driver is acceptable comprises:
      determining whether a cardiac arrest risk of the driver is within a certain cardiac threshold by automatically sampling a cardiac activity of the driver with an in-vehicle electrocardiogram detection component;
      in response to determining the cardiac arrest risk of the driver is within a certain cardiac threshold, determining whether an alcohol level in a breathing gas of the driver is below a certain alcohol threshold by automatically sampling the breathing gas of the driver using an alcohol detection component;
      in response to determining the alcohol level of the driver is below the certain alcohol threshold, determining whether a body temperature of the driver is within a range of predetermined normal body temperatures by automatically sampling the body temperature of the driver using a body temperature detection component;
      in response to determining the body temperature of the driver is within the range of the predetermined normal body temperature, determining whether an eye expression of the driver indicates a risk of the driver is below a certain drowsiness threshold by sampling the eye expression of the driver using a photography component; and
      in response to determining the risk of the driver exceeds the certain drowsiness threshold, determining the physical status of the driver is not acceptable;
   determining, at the processor within the vehicle, whether the identity of the driver is acceptable using a second set of sensors, wherein the identity of the driver is acceptable when the second set of sensors indicate that the driver is an authorized driver, and wherein the second set of sensors include at least one of the following:

a fingerprint detection component configured to detect a fingerprint of the driver;
the electrocardiogram detection component configured to detect the cardiac activity of the driver; and
the photography component configured to detect an image of the driver; and
in response to the determination that the identity of the driver is acceptable and the determination that the physical status of the driver is not acceptable, activating, at the processor within the vehicle, an automatic driving system.

2. The method of claim 1, further comprising determining the physical status of the driver is unacceptable when the electrocardiogram detection component detects that the cardiac activity of the driver indicates that the likelihood of cardiac arrest of the driver exceeds a certain threshold.

3. The method of claim 2, wherein an electrocardiogram signal is extracted from the cardiac activity of the driver, and wherein the P wave, Q wave, R wave, S wave, and T wave are extracted from the electrocardiogram signal.

4. The method of claim 1, further comprising determining the physical status of the driver is unacceptable when the alcohol detection component detects that the breathing gas of the driver indicates that the blood alcohol content of the driver exceeds a certain threshold.

5. The method of claim 1, further comprising determining the physical status of the driver is determined to be unacceptable when the body temperature detection component detects that the body temperature of the driver is above or below certain thresholds.

6. The method of claim 1, further comprising determining the physical status of the driver is unacceptable when the photography component detects that the eye expression of the driver indicates that the likelihood of drowsiness exceeds a certain threshold.

7. The method of claim 1, wherein the identity of the driver is determined to be acceptable when the fingerprint detection component detects that the fingerprint of the driver matches a fingerprint stored in a server of acceptable driver fingerprints.

8. The method of claim 1, wherein the identity of the driver is determined to be acceptable when the electrocardiogram detection component detects that the cardiac activity of the driver matches a cardiac activity stored in a server of acceptable driver cardiac activities.

9. The method of claim 1, further comprising:
activating, at the processor within the vehicle, an alarm system when it is determined that the identity of the driver is unacceptable.

10. The method of claim 1, further comprising:
activating, at the processor within the vehicle, an automatic driving system when it is determined that the physical status of the driver is unacceptable.

11. A system configured to determine whether a driver is permitted to start a vehicle, the system comprising a processor configured to perform:
determining, at a processor within the vehicle, whether a physical status of the driver is acceptable using a first set of sensors, wherein the determining whether the physical status of the driver is acceptable comprises:
determining whether a cardiac arrest risk of the driver is within a certain cardiac threshold by automatically sampling a cardiac activity of the driver with an in-vehicle electrocardiogram detection component;
in response to determining the cardiac arrest risk of the driver is within a certain cardiac threshold, determining whether an alcohol level in a breathing gas of the driver is below a certain alcohol threshold by automatically sampling the breathing gas of the driver using an alcohol detection component;
in response to determining the alcohol level of the driver is below the certain alcohol threshold, determining whether a body temperature of the driver is within a range of predetermined normal body temperatures by automatically sampling the body temperature of the driver using a body temperature detection component;
in response to determining the body temperature of the driver is within the range of the predetermined normal body temperature, determining whether an eye expression of the driver indicates a risk of the driver is below a certain drowsiness threshold by sampling the eye expression of the driver using a photography component; and
in response to determining the risk of the driver exceeds the certain drowsiness threshold, determining the physical status of the driver is not acceptable;
determining, at the processor within the vehicle, whether the identity of the driver is acceptable using a second set of sensors, wherein the identity of the driver is acceptable when the second set of sensors indicate that the driver is an authorized driver, and wherein the second set of sensors include at least one of the following:
a fingerprint detection component configured to detect a fingerprint of the driver;
the electrocardiogram detection component configured to detect the cardiac activity of the driver; and
the photography component configured to detect an image of the driver; and
in response to determination that the identity of the driver is acceptable and the determination that the physical status of the driver is not acceptable, activating, at the processor within the vehicle, an automatic driving system.

12. The system of claim 11, wherein processor is further configured to perform determining the physical status of the driver is unacceptable when the electrocardiogram detection component detects that the cardiac activity of the driver indicates that the likelihood of cardiac arrest of the driver exceeds a certain threshold.

13. The system of claim 12, wherein an electrocardiogram signal is extracted from the cardiac activity of the driver, and wherein the P wave, Q wave, R wave, S wave, and T wave are extracted from the electrocardiogram signal.

14. The system of claim 11, processor is further configured to perform determining the physical status of the driver is unacceptable when the alcohol detection component detects that the breathing gas of the driver indicates that the blood alcohol content of the driver exceeds a certain threshold.

15. The system of claim 11, processor is further configured to perform the physical status of the driver is unacceptable when the body temperature detection component detects that the body temperature of the driver is above or below certain thresholds.

16. The system of claim 11, wherein the physical status of the driver is determined to be unacceptable when the photography component detects that the eye expression of the driver indicates that the likelihood of drowsiness exceeds a certain threshold.

17. The system of claim 11, wherein the identity of the driver is determined to be acceptable when the fingerprint detection component detects that the fingerprint of the driver matches a fingerprint stored in a server of acceptable driver fingerprints.

18. The system of claim 11, wherein the identity of the driver is determined to be acceptable when the electrocardiogram detection component detects that the cardiac activity of the driver matches a cardiac activity stored in a server of acceptable driver cardiac activities.

19. The system of claim 11, wherein the processor is further configured to perform:
   activating an alarm system when it is determined that the identity of the driver is unacceptable.

20. A method for determining whether a driver is permitted to start a vehicle, the method comprising:
   determining, at a processor within the vehicle, a driver in the vehicle is authorized;
   in response to the determination that the driver in the vehicle is authorized, determining, at the processor within the vehicle, determining whether a physical status of the driver is acceptable using a first set of sensors, wherein the determining whether the physical status of the driver is acceptable comprises:
      determining whether a cardiac arrest risk of the driver is within a certain cardiac threshold by automatically sampling a cardiac activity of the driver with an in-vehicle electrocardiogram detection component;
      in response to determining the cardiac arrest risk of the driver is within a certain cardiac threshold, determining whether an alcohol level in a breathing gas of the driver is below a certain alcohol threshold by automatically sampling the breathing gas of the driver using an alcohol detection component;
      in response to determining the alcohol level of the driver is below the certain alcohol threshold, determining that a body temperature of the driver is within a range of predetermined normal body temperatures by automatically sampling the body temperature of the driver using a body temperature detection component;
      in response to determining the body temperature of the driver is within the range of the predetermined normal body temperature, determining that an eye expression of the driver indicates a risk of the driver is below a certain drowsiness threshold by sampling the eye expression of the driver using a photography component; and
      in response to determining the risk of the driver exceeds the certain drowsiness threshold, determining the physical status of the driver is not acceptable;
   in response to the determination that the driver in the vehicle is authorized and the determination that the physical status of the driver is acceptable, starting the vehicle;
   in response to determination that the identity of the driver is acceptable and the determination that the identity of the driver is not acceptable, disallowing, at the processor within the vehicle, the vehicle from being started.

* * * * *